United States Patent
Baker, Jr.

(10) Patent No.: US 9,131,878 B2
(45) Date of Patent: Sep. 15, 2015

(54) ADJUSTING PARAMETERS USED IN PULSE OXIMETRY ANALYSIS

(75) Inventor: Clark R. Baker, Jr., Castro Valley, CA (US)

(73) Assignee: COVIDIEN LP, Mansfield, MA (US)

( * ) Notice: Subject to any disclaimer, the term of this patent is extended or adjusted under 35 U.S.C. 154(b) by 556 days.

(21) Appl. No.: 13/548,008

(22) Filed: Jul. 12, 2012

(65) Prior Publication Data

US 2012/0277595 A1     Nov. 1, 2012

Related U.S. Application Data

(63) Continuation of application No. 12/483,810, filed on Jun. 12, 2009, now Pat. No. 8,238,994, which is a continuation of application No. 11/261,012, filed on Oct. 28, 2005, now abandoned.

(51) Int. Cl.
| | | |
|---|---|---|
| *A61B 5/145* | (2006.01) | |
| *A61B 5/024* | (2006.01) | |
| *A61B 5/1455* | (2006.01) | |
| *A61B 5/00* | (2006.01) | |

(52) U.S. Cl.
CPC .............. *A61B 5/14546* (2013.01); *A61B 5/024* (2013.01); *A61B 5/14551* (2013.01); *A61B 5/7221* (2013.01)

(58) Field of Classification Search
CPC ............... A61B 5/024; A61B 5/14546; A61B 5/14551; A61B 5/7221
See application file for complete search history.

(56) References Cited

U.S. PATENT DOCUMENTS

| | | | |
|---|---|---|---|
| 4,911,167 A * | 3/1990 | Corenman et al. | 600/324 |
| 4,960,126 A | 10/1990 | Conlon et al. | |
| 5,020,540 A | 6/1991 | Chamoun | |
| 5,827,195 A | 10/1998 | Lander | |
| 6,018,673 A | 1/2000 | Chin et al. | |
| 6,293,915 B1 | 9/2001 | Amano et al. | |
| 6,339,715 B1 | 1/2002 | Bahr et al. | |
| 6,374,129 B1 | 4/2002 | Chin et al. | |
| 6,516,209 B2 | 2/2003 | Cheng et al. | |
| 6,647,280 B2 | 11/2003 | Bahr et al. | |
| 6,845,256 B2 | 1/2005 | Chin et al. | |
| 6,879,850 B2 | 4/2005 | Kimball | |
| 7,039,538 B2 | 5/2006 | Baker, Jr. | |
| 7,090,648 B2 | 8/2006 | Sackner et al. | |
| 7,107,116 B2 | 9/2006 | Geng | |
| 7,194,293 B2 | 3/2007 | Baker, Jr. | |
| 7,209,774 B2 | 4/2007 | Baker, Jr. | |
| 7,225,013 B2 | 5/2007 | Geva et al. | |
| 7,242,997 B2 | 7/2007 | Geng | |
| 7,254,500 B2 | 8/2007 | Makeig et al. | |
| 7,260,425 B2 | 8/2007 | Chin et al. | |
| 7,268,873 B2 | 9/2007 | Sevick-Muraca et al. | |

(Continued)

FOREIGN PATENT DOCUMENTS

| | | |
|---|---|---|
| WO | 2005025399 | 3/2005 |
| WO | 2006097437 | 9/2006 |
| WO | 2006110488 | 10/2006 |

*Primary Examiner* — Eric Winakur
(74) *Attorney, Agent, or Firm* — Fletcher Yoder PC

(57) ABSTRACT

Adjusting a pulse qualification criterion includes receiving a signal representing a plurality of pulses, where the signal is generated in response to detecting light scattered from blood perfused tissue. A characteristic is determined. A pulse qualification criterion used for qualifying a pulse is adjusted in accordance with the characteristic. The pulses are evaluated according to the pulse qualification criterion.

20 Claims, 4 Drawing Sheets

(56) References Cited

U.S. PATENT DOCUMENTS

| | | |
|---|---|---|
| 7,301,630 B2 | 11/2007 | Furukawa |
| 7,392,075 B2 | 6/2008 | Baker, Jr. |
| 7,474,907 B2 | 1/2009 | Baker, Jr. |
| 2002/0103423 A1 | 8/2002 | Chin et al. |
| 2004/0034293 A1 | 2/2004 | Kimball |
| 2005/0070773 A1 | 3/2005 | Chin et al. |
| 2005/0070775 A1 | 3/2005 | Chin et al. |
| 2005/0113656 A1 | 5/2005 | Chance |
| 2005/0197552 A1 | 9/2005 | Baker, Jr. |
| 2005/0197579 A1 | 9/2005 | Baker, Jr. |
| 2005/0197793 A1 | 9/2005 | Baker, Jr. |
| 2006/0195280 A1 | 8/2006 | Baker, Jr. |
| 2007/0100220 A1 | 5/2007 | Baker, Jr. |
| 2007/0299328 A1 | 12/2007 | Chin et al. |
| 2008/0076986 A1 | 3/2008 | Pav |
| 2008/0082018 A1 | 4/2008 | Sackner et al. |
| 2008/0255436 A1 | 10/2008 | Baker |

* cited by examiner

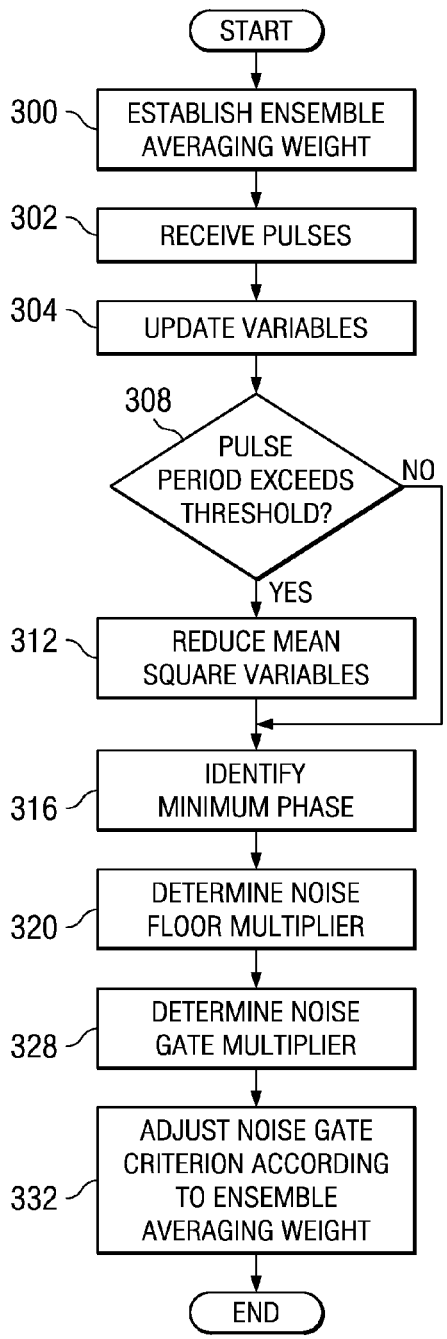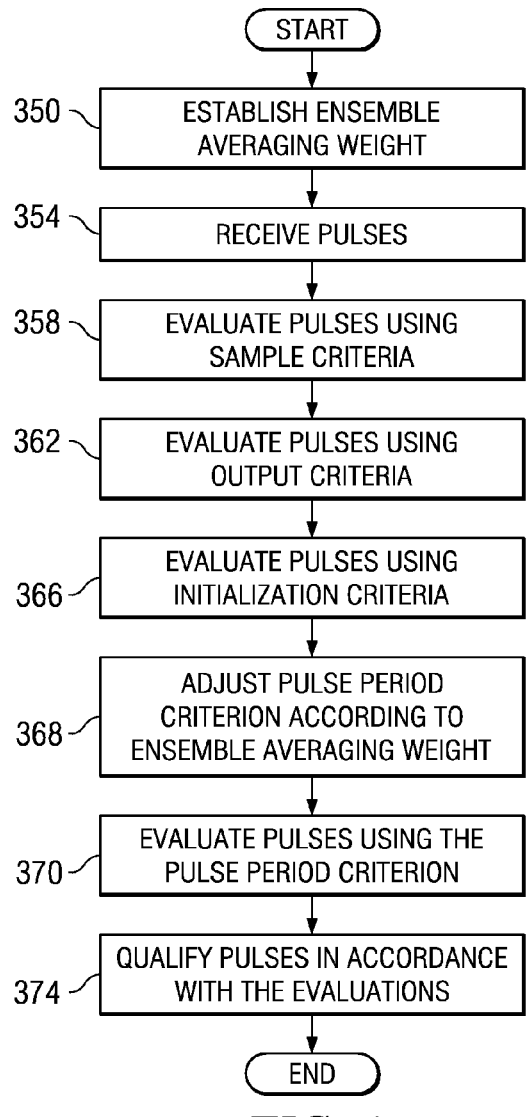
FIG. 3
FIG. 4

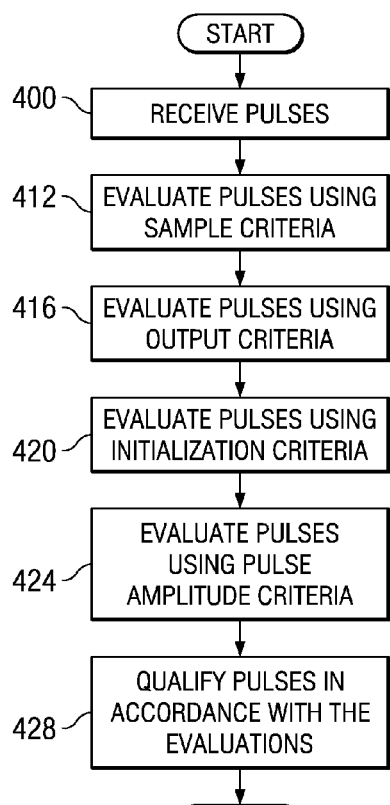
FIG. 5
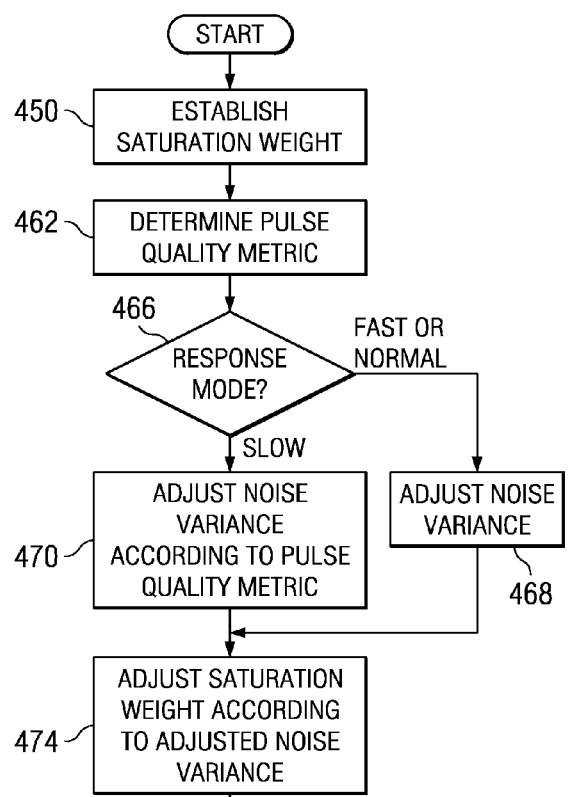
FIG. 6
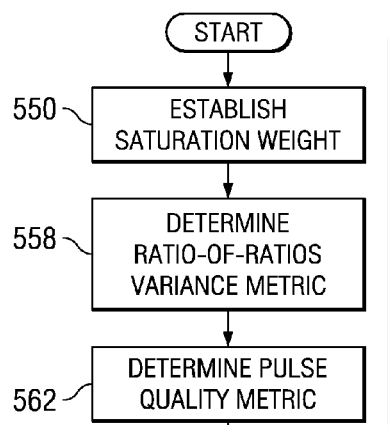
FIG. 7
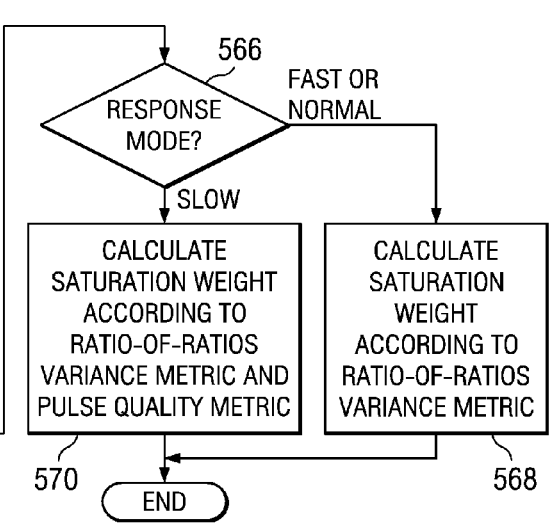

ADJUSTING PARAMETERS USED IN PULSE OXIMETRY ANALYSIS

RELATED APPLICATIONS

This application is a continuation of U.S. application Ser. No. 12/483,810 filed on Jun. 12, 2009, which is a continuation of U.S. application Ser. No. 11/261,012 filed on Oct. 28, 2005, now abandoned, which are each incorporated herein by reference in their entirety.

TECHNICAL FIELD

This invention relates generally to the field of medical devices and, more particularly, to adjusting parameters used in pulse oximetry analysis.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

A pulse oximeter is a medical device that may be used to measure various blood characteristics, for example, the oxygen saturation of hemoglobin in pulsing blood and/or the pulse rate of a patient. To measure these characteristics, a non-invasive sensor may be used to pass light through a portion of blood perfused tissue and photo-electrically sense the absorption and scattering of light in the tissue. The amount of light absorbed and/or scattered is analyzed to estimate the amount of blood constituent in the tissue.

A detector signal resulting from measurement of the light describes the blood characteristics. As an example, pulses refer to the varying amount of arterial blood present in the tissue during a cardiac cycle. The varying amount of arterial blood yields cyclic attenuation of the light passing through the tissue. Accordingly, the detector signal from measurement of the light exhibits the familiar plethysmographic waveform.

Analysis of detector signals involves processes that use various parameters. As an example, the analysis may involve filtering estimates of hemoglobin saturation to improve the accuracy of the saturation estimates. As another example, the analysis may involve filtering of plethysmographic waveforms. The filtering may use parameters such as filter weights or coefficients to adjust the filtering process. As another example, the analysis may involve applying pulse qualification criteria to qualify or disqualify pulses. The pulse qualification criteria may include parameters used to adjust the pulse qualification.

It is desirable to provide a flexible and robust methodology for adjusting the parameters of oximetry analysis.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In accordance with one aspect of the present invention, there is provided a method for adjusting a pulse qualification criterion. The method may include receiving a signal representing a plurality of pulses, where the signal is generated in response to detecting light scattered from blood perfused tissue. A filter parameter value of a filter parameter of a filter may be determined, where the filter may be operable to filter the signal. A pulse qualification criterion may be adjusted in accordance with the filter parameter value, where the pulse qualification criterion may be used for qualifying a pulse. The pulses may be evaluated according to the pulse qualification criterion.

In accordance with another aspect of the present invention, there is provided a method for adjusting a pulse qualification criterion. The method may include receiving a signal representing a plurality of pulses, where the signal may be generated in response to detecting light scattered from blood perfused tissue. Each pulse may have an amplitude and a period, and a subset of the pulses may have a plurality of amplitudes and a plurality of periods. An average amplitude may be determined from the plurality of amplitudes, and an average period may be determined from the plurality of periods. A pulse qualification criterion may be adjusted in accordance with the average amplitude and the average period. Pulses may be evaluated according to the pulse qualification criterion.

In accordance with another aspect of the present invention, there is provided a method for adjusting a filter weight of a saturation filtering process. The method may include receiving a signal representing a plurality of pulses, where the signal may be generated in response to detecting light scattered from blood perfused tissue. The light may comprise a red waveform and an infrared waveform. A ratio-of-ratios variability metric indicating the variation of a ratio-of-ratios may be determined. A ratio-of-ratios may represent the ratio of absorbances of the red waveform and the infrared waveform. A pulse quality metric indicating the quality of one or more pulses may be determined A saturation filter weight may be adjusted in accordance with the ratio-of-ratios variability metric and the pulse quality metric, where the saturation filter weight may represent a weight used for a filtering process operable to filter a saturation estimate of the blood perfused tissue.

BRIEF DESCRIPTION OF THE DRAWINGS

Certain exemplary embodiments are described in the following detailed description and in reference to the drawings in which:

FIG. 3 is a flowchart illustrating one embodiment of a method for adjusting a noise gate parameter of a noise gate criterion in accordance with an ensemble averaging weight;

FIG. 4 is a flowchart illustrating one embodiment of a method for adjusting a pulse period criterion in accordance with an ensemble averaging weight;

FIG. 5 is a flowchart illustrating one embodiment of a method for adjusting a pulse amplitude criterion in accordance with an average pulse amplitude and an average pulse period;

FIG. 6 is a flowchart illustrating one embodiment of a method for adjusting a saturation weight in accordance with a pulse quality metric; and FIG. 7 is a flowchart illustrating an embodiment of a method for adjusting a saturation weight in accordance with a ratio-of-ratios variability metric and a pulse quality metric.

DETAILED DESCRIPTION

The exemplary embodiments described below are best understood by referring to FIGS. 1 through 6 of the drawings, like numerals being used for like and corresponding parts of the various drawings. The methods and systems in accordance with these exemplary embodiments are directed towards adjusting parameters of oximetry analysis. These embodiments may be particularly applicable to and thus, are explained by reference to measuring oxygen saturation and qualifying pulses, as applicable to pulse oximeter monitors and pulse oximetry sensors. It should be realized, however, that the embodiments may be applicable to any generalized patient monitor and associated patient sensor, such as, for example, an electrocardiograph (ECG), blood pressure monitor, etc., and are thus, also applicable to nonoximetry methods and systems.

Figure 1:
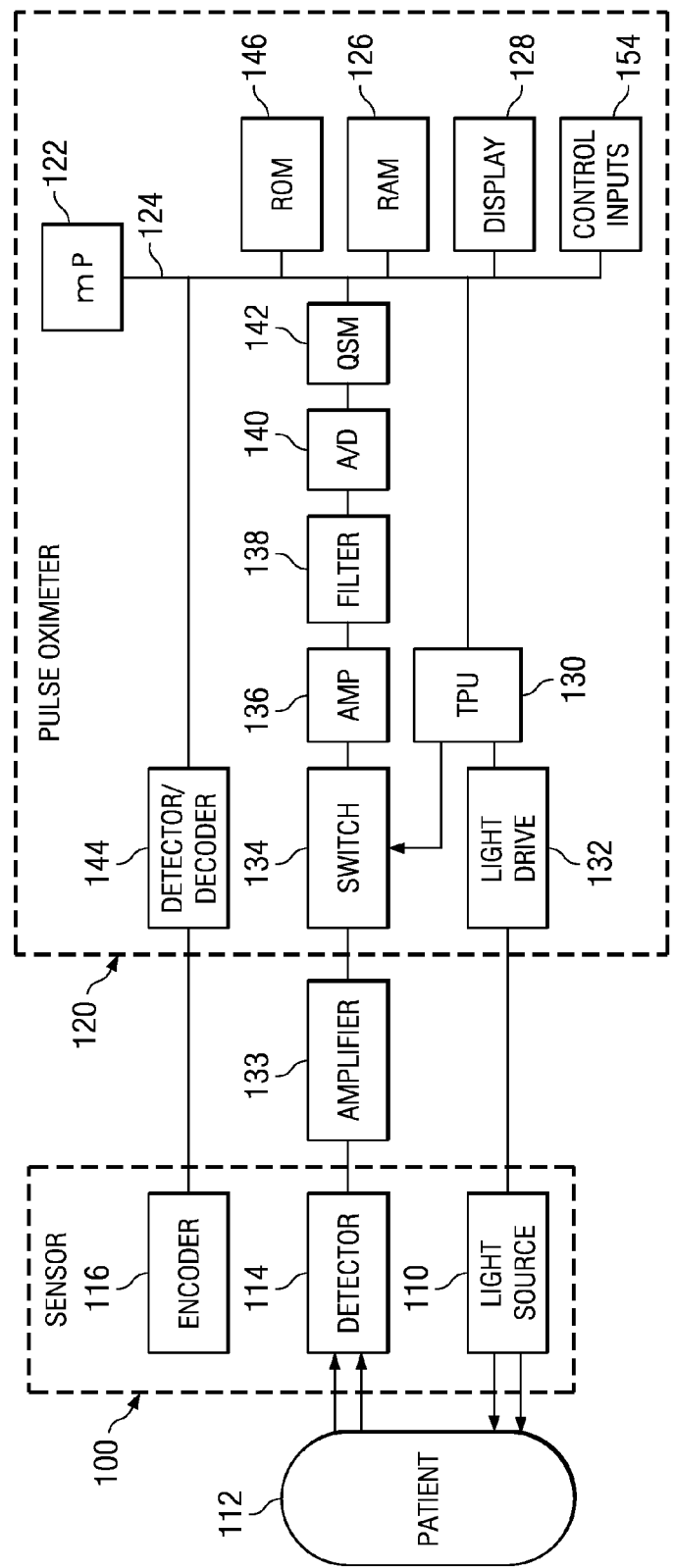
FIG. 1 is a block diagram of one embodiment of a pulse oximeter that may be configured to implement embodiments of the present invention.

FIG. 1 is a block diagram of one embodiment of a pulse oximeter that may be configured to implement certain techniques, as described in detail below. The techniques may be implemented as a data processing procedure that is executed by a oximeter 120 having a microprocessor 122, as described below. A sensor 100 illuminates blood perfused tissue 112, detects light scattered by tissue 112, and generates detector signals. According to the illustrated embodiment, sensor 100 may comprise a light source 110, a photodetector 114, and an encoder 116. Light from light source 110 passes into blood perfused tissue 112. Photodetector 114 detects the scattered light and generates detector signals representing the detected light. Encoder 116 provides signals indicative of the wavelength of light source 110 to allow the oximeter 120 to select appropriate calibration coefficients for calculating oxygen saturation.

Pulse oximeter 120 analyzes the detector signals. According to the illustrated embodiment, pulse oximeter 120 includes general processing and interface components such as a microprocessor 122, a ROM 146, a RAM 126, a display 128, and control inputs 154 coupled to an internal bus 124. Pulse oximeter 120 also includes components that operate to control the light that passes through tissue 112. According to the illustrated embodiment, pulse oximeter 120 includes a time processing unit (TPU) 130 and light drive circuitry 132. TPU 130 provides timing control signals to light drive circuitry 132. Light drive circuitry 132 controls when light source 110 is illuminated, and may control multiplexed timing if multiple light sources 110 are used.

Signals from detector 114 are received through amplifier 133. Pulse oximeter 120 includes components that operate to process the received signal. According to the illustrated embodiment, pulse oximeter 120 includes a switching circuit 134, an amplifier 136, a low pass filter 138, an analog-to-digital converter 140, and a queued serial module (QSM) 142. Switching circuit 134 controls the sampling of the signals in response to instructions from TPU 130. If multiple light sources are used, the sampling times may depend upon which of the light sources 110 are illuminated.

The signals from the switch 134 are passed through amplifier 136, low pass filter 138, and analog-to-digital converter 140. Digital data from the signals is then stored in a queued serial module (QSM) 142. The digital data may be downloaded to RAM 126 as QSM 142 is filled. In one embodiment, there may be multiple parallel paths of separate amplifier, filter, and analog-to-digital converters for different light wavelengths.

Microprocessor 122 calculates oxygen saturation based on the values of the received signals. ROM 146 may store coefficients used in the calculations. Detector/decoder 144 selects the appropriate coefficients according to signals received from encoder 116. Control inputs 154 receive input data and instructions, and may comprise, for instance, a switch on the pulse oximeter, a keyboard, or a port providing instructions from a remote host computer. Display 128 provides feedback and results of the analysis.

One or more components of pulse oximeter 120 may include appropriate input devices, output devices, mass storage media, processors, memory, or other components for receiving, processing, storing, and communicating information according to the operation of pulse oximeter 120. As an example, one or more components of pulse oximeter 120 may include logic, an interface, memory, or any suitable combination of the preceding. By way of example, "logic" may refer to hardware, software, firmware, or any suitable combination of the preceding. Certain logic may manage the operation of a device, and may comprise, for example, a processor. "Processor" may refer to any suitable device operable to execute instructions and manipulate data to perform operations.

"Interface" may refer to logic of a device operable to receive input for the device, send output from the device, perform suitable processing of the input or output or both, or any combination of the preceding, and may comprise one or more ports, conversion software, or both. "Memory" may refer to logic operable to store and facilitate retrieval of information, and may comprise Random Access Memory (RAM), Read Only Memory (ROM), a magnetic drive, a disk drive, a Compact Disk (CD) drive, a Digital Video Disk (DVD) drive, removable media storage, any other suitable data storage medium, or a combination of any of the preceding.

Modifications, additions, or omissions may be made to pulse oximeter 120 without departing from the scope of the invention. The components of pulse oximeter 120 may be integrated or separated according to particular needs. Moreover, the operations of pulse oximeter 120 may be performed by more, fewer, or other modules. Additionally, operations of pulse oximeter 120 may be performed using any suitable logic comprising software, hardware, other logic, or any suitable combination of the preceding.

The brief description of an exemplary pulse oximeter set forth above, serves as a basis for describing the exemplary methods for adjusting oximetry parameters. Any suitable oximeter, however, may be used.

Figure 2:
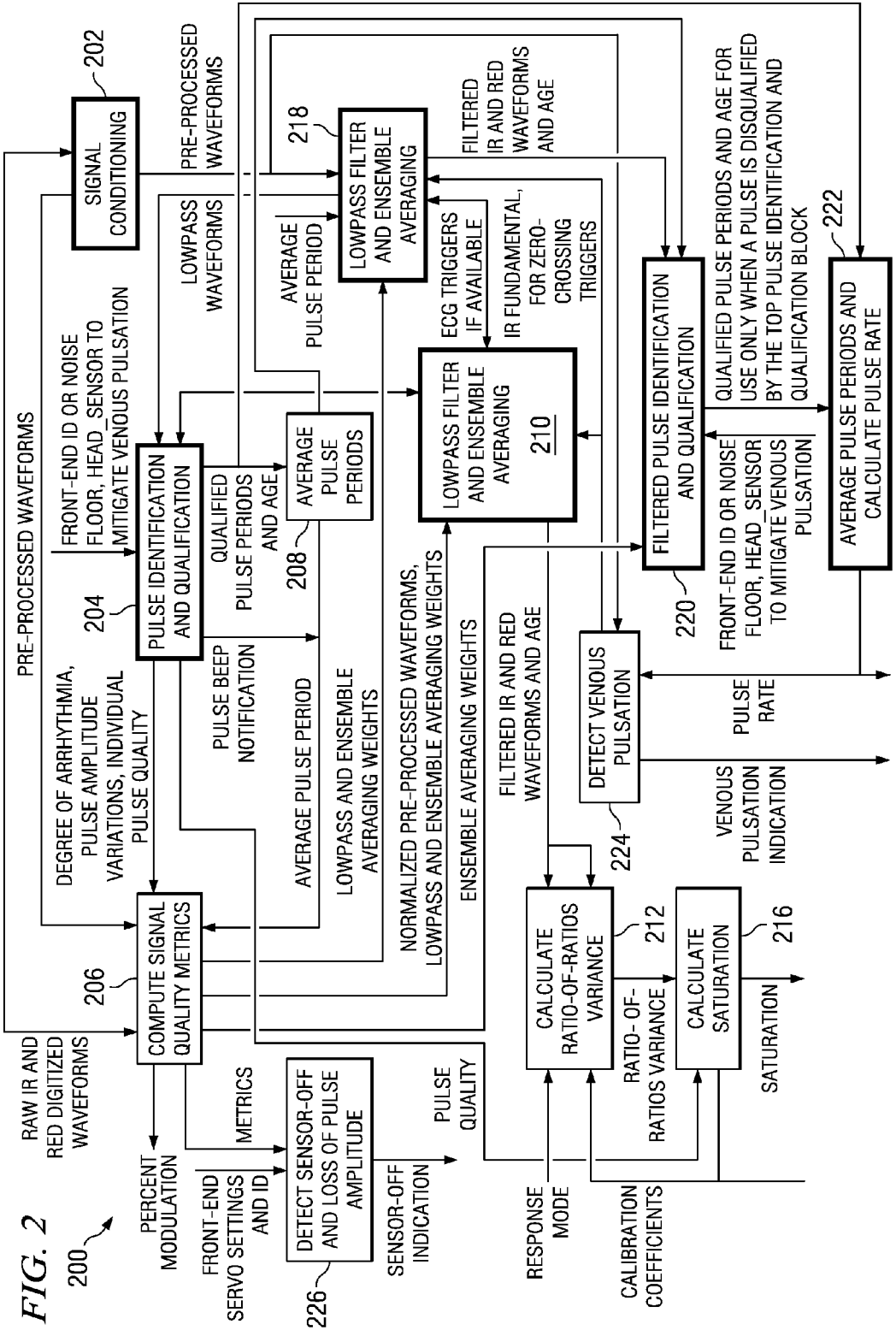
FIG. 2 is a block diagram of a signal processing system of a pulse oximeter in accordance with one embodiment of the present invention.

FIG. 2 is a block diagram of an exemplary signal processing system 200 of a pulse oximeter. Embodiments for carrying out the present techniques may be implemented as a part of a signal processing system, such as signal processing system 200, that processes optical signals for the purposes of operating a pulse oximeter. For example, signal processing system 200 may be implemented as a software process that is executed by a processor of a pulse oximeter, such as the processor 122 of the oximeter 120 discussed above.

Block 202 represents the operations of a Signal Conditioning subsystem. Block 202 may receive digitized Red and IR signals, and may output pre-processed Red and IR signals. The Signal Conditioning subsystem conditions signals to emphasize higher frequencies associated with the human plethysmograph and to attenuate lower frequencies associated with interference from noise sources. The derivative-filtered plethysmographs characteristically have a negative skewness. The signals may be conditioned by taking a first derivative to reduce or eliminate a baseline shift, and then low pass filtering with coefficients based on hardware characteristics. The Signal Conditioning subsystem may also divide the lowpass filtered values by the average of the respective IR or Red signals.

Block 204 represents the operations of a Pulse Identification and Qualification subsystem. Block 204 may receive pre-processed Red and IR signals, average pulse period, lowpass waveforms from the Signal Conditioning subsystem, and/or ensemble averaging filter weights. Block 204 may output pulse quality of individual pulses, degree of arrhythmia, pulse amplitude variations, and/or qualified pulse periods and age.

The Pulse Identification and Qualification subsystem identifies pulses and qualifies the pulses as likely arterial pulses. Pulses may be identified and qualified by applying a pre-trained neural net to the IR signals and/or Red signals. Signal metrics describing pulses may be compared with pulse qualification criteria in order to qualify the pulses. A signal metric represents a feature of a signal, and it may be used to classify a signal. For example, a signal metric may be used to qualify a signal. Example signal metrics may describe features of individual pulses, such as amplitude, period, shape, ratio-of-ratios, and/or rise time. Example signal metrics may describe features of a sequence of pulses such as the variability of the features of individual pulses (e.g., period variability).

A pulse qualification criterion may include parameters with which the signal quality metrics may be compared. The parameters may be adjusted in response to variables such as filter parameters or signal metrics. A filter parameter may refer to a parameter of a filter that may be modified to change the filtering. An example embodiment of a method that adjusts parameters in response to filter parameters is described with reference to FIGS. 3 and 4. An example embodiment of a method that adjusts parameters in response to signal quality metrics is described with reference to FIG. 5.

Block 206 represents operations that compute signal quality metrics. Block 206 may receive: raw digitized Red and IR signals; degree of arrhythmia, individual pulse quality, pulse amplitude variation; pre-processed Red and IR signals; and/or average pulse period. Block 206 may output lowpass and ensemble averaging filter weights, normalized pre-processed waveforms, and/or percent modulation. The signal quality metrics may be used to set parameters for other processes.

Block 208 represents operations that compute the average pulse period from the received pulses. Block 208 may receive qualified pulse periods and age, and it may output the average pulse period.

Block 210 represents the operations of a Lowpass Filter and Ensemble Averaging subsystem. Block 210 may receive normalized pre-processed Red and IR signals, average pulse period, and/or low pass filter weights and ensemble averaging filter weights. Block 210 may output filtered Red and IR signals and/or age. The Lowpass Filter and Ensemble Averaging subsystem filters and ensemble averages normalized and preprocessed signals processed by block 206. Ensemble averaging may involve attenuating frequencies that are not of interest. For example, ensemble averaging may involve attenuating frequencies that are not at the estimated pulse rate or harmonic. The Lowpass Filter and Ensemble Averaging subsystem may also track the age of the signal and/or filtering results.

Block 212 represents operations that estimate the ratio-of-ratios variance for the filtered waveforms. Block 212 may receive filtered Red and IR signals, age, calibration coefficients, and/or response mode. Block 212 may output a ratio-of-ratios variance. A ratio-of-ratios is the ratio of the absorbances of the red and infrared signals. A ratio-of-ratios variability metric indicates the variation of a ratio-of-ratios. According to one embodiment, a ratio-of-ratios variance may be adjusted according to a signal metric and a ratio-of-ratios variability metric. An example method is described with reference to FIG. 6. Block 216 represents operations that calculate oxygen saturation. Block 216 may receive ratio-of-ratios variability metrics and/or calibration coefficients, and may output oxygen saturation values.

Block 218 represents the operations of a Low Pass Filter and Ensemble Averaging subsystem. Block 218 may operate in a substantially similar manner as block 210. Block 220 represents the operations of a Filtered Pulse Identification and Qualification subsystem. Block 220 may operate in a substantially similar manner as block 204. The Filtered Pulse Identification and Qualification subsystem calculates and qualifies the pulse periods from the filtered waveforms. The results from the subsystem may be used by block 222 if a pulse period is disqualified by block 204.

Block 222 represents the operations of an Average Pulse Periods and Calculate Pulse Rate subsystem. Block 222 may receive qualified pulse periods and age, and may output an average pulse period and/or a pulse rate.

Block 224 represents the operations that detect venous pulsation. Block 224 may receive the pre-processed Red and IR signals and age from block 202, and it may output pulse rate and an indication of venous pulsation. Block 226 represents the operations that detect sensor-off and loss of pulse amplitude.

Modifications, additions, or omissions may be made to system 200 without departing from the scope of the invention. The components of system 200 may be integrated or separated according to particular needs. Moreover, the operations of system 200 may be performed by more, fewer, or other modules. Additionally, operations of system 200 may be performed using any suitable logic comprising software, hardware, firmware, or any suitable combination of the preceding.

FIG. 3 is a flowchart illustrating one embodiment of a method for adjusting a noise gate parameter of a noise gate criterion in accordance with an ensemble averaging weight. Ensemble averaging filtering may reduce the noise level, which may allow for a lowered noise gate. Accordingly, the ensemble averaging weight, which indicates the degree of ensemble averaging, may be used to adjust the noise gate parameter.

The method starts at step 300, where an ensemble averaging weight is established. An ensemble averaging weight may refer to a weight value that is used to calculate a weighted average of new samples and previously ensemble averaged samples from a previous pulse period. Any suitable ensemble averaging weight may be used. According to one embodiment, Ensemble_Averaging_Weight used by the Ensemble Averaging subsystem may be used. If the pulses are not ensemble averaged, the weight may be set to default value, for example, Ensemble_Averaging_Weight=1.0.

Pulses are received at step 302. Variables describing the pulses are updated at step 304. The variables may be updated in any suitable manner. For example, the variables may be updated for each sample, prior to the every-potential-pulse, according to the following operations:

1. Baseline represents the average of input samples, and may be updated according to the following equation:

$$Baseline_t = Baseline_{t-1} + c_1 \Delta t * (Curr\_Sample - Baseline_{t-1})$$

where t represents a sample index, $c_1$ represents a constant, $\Delta t$ represents the sample interval given in seconds, Curr_Sample represents the current sample. Constant $c_1$ may be any suitable value, such as $c_1=0.01$ for a one-second response time, given sampling interval $\Delta t=10$ milliseconds.

2. Mean_Square represents the mean-square of input samples, and may be updated according to the following equation:

Mean_Square$_t$=Mean_Square$_{t-1}$+k*((Curr_Sample−Baseline)$^2$−Mean_Square$_{t-1}$)

where k represents a constant selected to yield a Mean_Square with a particular response time.

As an example, k may be determined according to the following equation to yield a Mean_Square with a response time of one second or one pulse, whichever is shorter:

$$k = \max\left(\frac{1}{\text{Avg\_Period}}, \Delta t\right), \text{ if Avg\_Period} > 0;$$

$$\max\left(\frac{1}{\text{Potential\_Pulse\_Period}}, \Delta t\right), \text{ if Potential\_Pulse\_Period} > 0,$$

AND previous Potential_Pulse_Period=0, AND Avg_Period=0; and $\Delta t$, if Avg_Period=0.

where Avg_Period represents the average pulse period, and Potential_Pulse_Period represents the pulse period of a potential pulse. A short response time may allow Mean_Square to decline quickly when a motion artifact ends, which may minimize the likelihood of ignoring real pulses. During the first potential pulse, the above equation for k may give equal weight to each sample for up to one second, which may prevent initial underestimates of Mean_Square$_t$ as it diverges from zero.

3. Gated RMS represents the square root of Mean Square, and may be updated according to the following equation:

$$\text{Gated\_RMS}_t = \begin{cases} \sqrt{\text{Mean\_Square}_t} & \text{if Curr\_Sample} > \text{Baseline}_t \\ \text{Gated\_RMS}_{t-1} & \text{if Curr\_Sample} \leq \text{Baseline}_t \end{cases}$$

At step 308, the pulse period may exceed a threshold that indicates that a pulse has just been missed or will occur shortly. The threshold may have any suitable value, such as two seconds. If the pulse period exceeds the threshold at step 308, the method proceeds to step 312, where mean square parameters are reduced. According to one embodiment, the mean square parameters may include Mean_Square and Gated_RMS, and may be reduced according to the following equations:

Gated_RMS$_t$=(1−$\Delta t$)Gated_RMS$_t$

Mean_Square$_t$=(1−$\Delta t$)Mean_Square$_t$

The method then proceeds to step 316. If the pulse period does not exceed the threshold at step 308, the method proceeds directly to step 316.

The minimum phase of a potential pulse is identified at step 316. The minimum phase may be identified when the value of Curr_Sample$_t$ has a specified relationship to previous or subsequent Curr_Sample$_t$ values. For example, a minimum phase may be identified when Curr_Sample$_t$ exceeds samples that occurred in the previous 100 to 150 milliseconds. Steps 320 through 332 describe updating the noise gate parameter of a noise gate criterion. A noise gate criterion may refer to a pulse qualification criterion that qualifies a pulse according to a noise gate. A noise gate parameter may refer to a parameter that controls the threshold that identifies whether a waveform includes noise. For example, the noise gate parameter may be adjusted to reduce the noise gate level if the ensemble averaging weight indicates an increased degree of ensemble averaging.

According to one embodiment, the noise gate parameter Noise_Gate may be defined according to the following equation:

Noise Gate=max(n*Gated_RMS, ($c_2$+$c_3$*E_A_W)*m*Noise_Floor/IR_DC)   4.

where n represents the noise gate multiplier, E_A_W represents Ensemble_Averaging_Weight, m represents a noise floor multiplier, IR_DC represents the current infrared (IR) A/D values, Noise_Floor represents a minimum noise level associated with the oximetry hardware, which determines a minimum value for the noise gate, and $c_2$ and $c_3$ represent any suitable constants, for example, $c_2=c_3=0.5$.

The noise floor multiplier of the noise gate parameter is set at step 320. The noise floor multiplier may be set in any suitable manner. As an example, noise floor multiplier m may initially be set to an unit value, for example, m=1.0. Subsequent values of noise floor multiplier m may be set according to the following equation:

$$m = 1 - \frac{c_4 * (c_5 * \text{Avg\_Period} - |\text{Avg\_Period} - \text{Pulse\_Period}|)}{c_5 * \text{Avg\_Period}},$$

if |Avg_Period−Pulse_Period| < $c_5$ * Avg_Period;

$$1 - \frac{c_4 * (c_5 * \text{Avg\_Period} - |\text{Avg\_Period} - \text{Potential\_Pulse\_Period}|)}{c_5 * \text{Avg\_Period}},$$

if |Avg_Period−Potential_Pulse_Period| < $c_5$ * Avg_Period;

and $$1 + \frac{c_4 * l}{c_5 * \text{Avg\_Period}},$$

if Potential_Pulse_Period < $c_6$ * Avg_Period.

where Pulse_Period represents the pulse period of the current pulse, l represents a parameter, and $c_4$, $c_5$, and $c_6$ represent constants having any suitable values, for example, $c_4=0.5$, $c_5=0.25$, and $c_6=0.75$.

Parameter l may be given by the following equation:

l=w((1−$c_5$)*Avg_Period−Potential_Pulse_Period)+(1−w)*($c_5$*Avg_Period−min(|$c_4$*Avg_Period−Potential_Pulse_Period|, $c_5$*Avg_Period))

where:

w=(Frequency_Ratio−$c_7$)/$c_8$ w=max(0, min(1, w))

and where Frequency_Ratio represents the frequency content of plethysmograph relative to the pulse rate, and $c_7$ and $c_8$ represent constants having any suitable values, for example, $c_7=1.25$ and $c_8=0.60$.

According to one embodiment, if Avg_Period is zero, then noise floor multiplier m may be calculated using the previous Potential_Pulse_Period in place of Avg_Period, provided that the previous Potential_Pulse_Period is acceptable for modifying noise floor multiplier m. For example, the duration of the previous Potential_Pulse_Period may be required to satisfy a threshold indicating that the pulse periods are less likely to reflect noise. According to the example, if Avg_Period is zero, then Mean_Square is established according to the following equation:

$$\text{Mean\_Square}_t = \max(\text{Mean\_Square}_t, c_9 * \text{Potential\_Pulse\_Amp}^2)$$

where Potential_Pulse_Amp represents the amplitude of a pulse, and $c_9$ represents a constant having any suitable value, for example, $c_9 = 0.12$. Potential_Pulse_Amp may be given as Potential_Pulse_Amp=Potential_Pulse_Max−Potential_Pulse_Min, where Potential_Pulse_Max represents the maximum of the previous several samples at the end of the maximum phase preceding the minimum phase, and Potential_Pulse_Min represents the minimum of the previous several samples at the end of the minimum phase.

The noise gate multiplier n is established at step 328. Noise gate multiplier n may be established in any suitable manner. According to one embodiment, noise gate multiplier n may be established according to the following equation:

$$n = c_{10} * m * \text{bound}(c_{11} + \text{Potential\_Pulse\_Skew}, c_{12}, c_{13}),$$
if Pulse_Period>Potential_Pulse_Period;

$$c_{10} * m * \text{bound}(c_{14} + \text{Potential\_Pulse\_Skew}, c_{12}, c_{13}), \text{ if}$$
Skew_Derivative Input Weight>$c_{15}$; and $$c_m * m \text{ otherwise.}$$

where Skew_Derivative_Input_Weight represents a weight used to combine the Curr_Sample waveform with its derivative to obtain a waveform having a more negative skew, Potential_Pulse_Skew represents the skewness of the samples in this combined waveform over the duration of the Potential Pulse Period, and $c_{10}$, $c_{11}$, $c_{12}$, $c_{13}$, $c_{14}$, and $c_{15}$ represent constants having any suitable values, for example, $c_{10} = 0.85$, $c_{11} = 1.5$, $c_{12} = -0.4$, $c_{13} = 1.0$, $c_{14} = 2.0$, and $c_{15} = 8.0$. notation bound(a, b, c) is used to denote min(max(a, b), c).

The noise gate parameter is adjusted according to the noise floor multiplier and the noise gate multiplier at step 332. After updating the noise gate parameter, the method ends.

Modifications, additions, or omissions may be made to the method without departing from the scope of the invention. The method may include more, fewer, or other steps. Additionally, steps may be performed in any suitable order without departing from the scope of the invention.

FIG. 4 is a flowchart illustrating one embodiment of a method for adjusting a pulse period criterion in accordance with an ensemble averaging weight. According to the embodiment, an ensemble averaging weight may indicate that a qualified pulse is not likely to have a pulse period that is substantially shorter than an average pulse period. Accordingly, a pulse period criterion may be adjusted to disqualify a pulse having a pulse period that is substantially shorter than an average pulse period.

The method starts at step 350, where an ensemble averaging weight is established. Pulses are received at step 354. Steps 358 through 370 describe evaluating the received pulses in accordance with pulse qualification criteria. The pulse qualification criteria may be applied in any suitable order. According to one embodiment, the pulse qualification criteria are applied in the order of the steps, and if a pulse fails one criterion, subsequent criteria are not applied.

Pulse qualification criteria comprising one or more sample criteria are applied at step 358. Any suitable sample criteria $SC_i$ may be used, for example:

$SC_1$: Pulse_Min<Pulse_Avg<Pulse_Max
$SC_2$: Avg_Min<Pulse_Avg<Pulse_Max where Pulse_Min represents the minimum of the previous several samples at the end of the minimum phase, Pulse_Avg represents the average of the samples of a period, and Pulse_Max represents the maximum of the previous several samples at the end of the maximum phase. Pulse_Avg may be expressed as $$\text{Pulse\_Avg} = \frac{\text{Pulse\_Sum}}{\text{Pulse\_Period}},$$

where Pulse_Sum represents the sum of the samples of a pulse, and Pulse_Period represents the pulse period of the current pulse. Pulse_Sum may be updated at every sample and reset to zero after calculating Pulse_Avg.

Pulse qualification criteria comprising one or more output criteria are applied at step 362. Any suitable output criteria $OC_i$ may be used, for example:

$OC_1$: Pulse_Qual_NN_Output$_t$>NN_Thresh
$OC_2$: Pulse_Qual_$_{Output}$_Integral$_t \geq c_8$, if no pulses have been qualified yet where Pulse_Qual_NN_Output represents the output of the pre-trained pulse qualification neural net, NN_Thresh represents a neural net threshold that may be used to qualify a pulse, Pulse_Qual_Output_Integral represents the integral of Pulse_Qual_NN Output$_t$, and $c_8$ represents a constant. The output of the neural net may range from 0 to 1.

In one example, NN_Thresh may be given by the following equation:

$$\text{NN\_Thresh} = c_1 + c_2 * (\text{Period\_Ratio} - c_3); \text{ and}$$

$c_4$, if there are no qualified pulses, for example, if Avg_Period=0 where Period_Ratio represents the ratio of the current period and the average period, and $c_1$, $c_2$, $c_3$, and $c_4$ represent constants having any suitable values, for example, $c_1 = 0.4$, $c_2 = 0.25$, $c_3 = 1.0$, and $c_4 = 0.5$. Period_Ratio may be given as $$\text{Period\_Ratio} = \min\left(2, \max\left(\frac{\text{Pulse\_Period}}{\text{Avg\_Period}}, \frac{\text{Avg\_Period}}{\text{Pulse\_Period}}\right)\right).$$

In one example, Pulse_Qual_Output Integral may be given by the following equation:

$$\text{Pulse\_Qual\_Output\_Integral}_t = \min(\text{Pulse\_Qual\_Output\_Integral}_{t-1} + \text{Pulse\_Qual\_NN\_Output}_t - c_5, c_6); \text{ and}$$

0, if Pulse_Qual_NN_Output$_t \leq c_7$ where $c_5$, $c_6$, and $c_7$ represent constants having any suitable values, for example, $c_5 = 0.5$, $c_6 = 100$, and $c_7 = 0.5$, and the subscript $t_{-1}$ denotes the previous pulse. In one example, constant $c_8$ may be set such that the initial estimate for Avg_Period is determined from either a very good pulse (for example, >95% probability of being an arterial pulse) or multiple acceptable successive pulses.

Pulse qualification criteria comprising one or more initialization criteria are applied at step 366. Any suitable initialization criterion $IC_i$ may be used, for example:

$IC_i$: |Pulse_Period-Last_Pulse_Period|$\leq c_9$*Initial_Pulse_Count*Pulse_Period where Pulse_Period represents the pulse period of the current pulse,
Last_Pulse_Period represents the Pulse_Period for the previous non-ignored pulse,
Initial_Pulse_Count represents the number of non-ignored pulses found since re-initialization, and $c_9$ represents a constant having any suitable value, for example, $c_9$=0.1. Initial_Pulse_Count may be incremented after a pulse is evaluated according to the pulse qualification criteria. Criterion $IC_1$ requires that consecutive pulse periods agree closely, but gradually relaxes its threshold with each successive pulse, which may reduce or prevent inaccurate initial pulse estimates. According to one embodiment, the first pulse may be rejected by requiring Initial_Pulse_Count>1.

$IC_2$: Path_Ratio<$c_{10}$, if no pulses have been qualified yet where Path_Ratio represents the ratio of the path length and the pulse amplitude, and $c_{10}$ represents a constant having any suitable value. Path_Ratio may be given by $$\frac{Path\_Length}{Pulse\_Max\text{-}Pulse\_Min},$$

where Path_Length represents the sum of sample-to-sample differences for the samples of a pulse. Constant $c_{10}$ may be selected to reduce the likelihood of initializing the pulse-rate estimate to values that are too low under noisy conditions. For example, $c_{10}$=4.0.

A pulse period criterion is adjusted according to the ensemble averaging weight at step 368. A pulse period criterion may refer to a pulse qualification criterion that qualifies a pulse according to a pulse period. Any suitable pulse period criterion $PPC_i$ may be used. According to one embodiment, a pulse with a shorter-than-average period may be disqualified if the ensemble averaging weight indicates that qualified pulses are less likely to have shorter-than-average period. As an example, pulse period criterion $PPC_1$ may be used and adjusted according to the following:

$PPC_1$: (Avg_Period−Pulse_Period)≤2*Avg_Period*min(Ensemble_Averaging_Weight$_t$, Ensemble_Averaging_Weight$_{t-1}$), if Avg_Period>0 where Avg_Period represents an estimate of the average pulse period, Pulse_Period represents the pulse period of the current pulse. Pulse qualification criteria comprising the pulse period criterion are applied at step 370.

The pulses are qualified or disqualified according to the evaluations at step 374. The pulses may be qualified or disqualified according to the evaluations in any suitable manner. According to one embodiment, a pulse that satisfies the above pulse qualification criteria is designated as qualified, and a pulse that fails to satisfy any of the above pulse qualification criteria is designated as non-qualified. After qualifying the pulses, the method ends.

Modifications, additions, or omissions may be made to the method without departing from the scope of the invention. The method may include more, fewer, or other steps. Additionally, steps may be performed in any suitable order without departing from the scope of the invention.

FIG. 5 is a flowchart illustrating one embodiment of a method for adjusting a pulse amplitude criterion in accordance with an average pulse amplitude and an average pulse period. According to one embodiment, a pulse amplitude criterion may disqualify a pulse with an amplitude that is much smaller than (e.g., more than three times smaller) an average amplitude and a period that is much greater that an average period. The pulse amplitude criterion may reduce the likelihood of qualifying instrument noise when the pulse amplitude suddenly disappears.

The method starts at step 400, where pulses are received. Steps 412 through 424 describe evaluating the received pulses in accordance with pulse qualification criteria. The pulse qualification criteria may be applied in any suitable order. According to one embodiment, the pulse qualification criteria are applied in the order of the steps, and if a pulse fails one criterion, subsequent criteria are not applied.

Pulse qualification criteria comprising one or more sample criteria are applied at step 412. Any suitable sample criterion $SC_i$ may be used, for example, $SC_1$ and $SC_2$. Pulse qualification criteria comprising one or more output criteria are applied at step 416. Any suitable output criterion $OC_i$ may be used, for example, $OC_1$ and $OC_2$. Pulse qualification criteria comprising one or more initialization criteria are applied at step 420. Any suitable initialization criterion $IC_i$ may be used, for example, $IC_1$ and $IC_2$.

Pulse qualification criteria comprising one or more pulse amplitude criteria are applied at step 424. Any suitable pulse amplitude criterion $PSC_i$ may be used. According to one embodiment, a pulse amplitude criterion may disqualify a pulse with an amplitude that is much smaller than (e.g., more than three times smaller) an average amplitude and a period that is much greater that an average period. The pulse amplitude criterion may reduce the likelihood of qualifying instrument noise when the pulse amplitude suddenly disappears.

An example pulse amplitude criterion $PSC_i$ may be expressed as:

$PSC_1$: Sum_Amp_Diff≥−$c_1$; OR
Period_Ratio≤$c_2$; OR
Period_Ratio≤($c_1$+Sum_Amp_Diff|$c_3$), provided that Pulse_Period>Avg_Period, pulses have been previously qualified, and a significant number of pulses have been previously evaluated;

where Sum_Amp_Diff represents the sum of amplitudes, Period_Ratio represents the ratio of the current period and the average period, and $c_1$, $c_2$, and $c_3$ represent constants having any suitable values, for example, $c_1$=2.3, $c_2$=1.3, and $c_3$=6.

According to one embodiment, Sum_Amp_Diff may be defined according to the following equation:

$$Sum\_Amp\_Diff = Amp\_Diff2_t + Amp\_Diff2_{t-1}$$

where:

$$Amp\_Diff2 = \ln(Pulse\_Amp_t) | Avg\_Ln\_Pulse\_Amp_t$$

where Avg_Ln_Pulse Amp represents a variable-weight filtered version of ln(Pulse_Amp), with a low initial value, and Pulse Amp represents the amplitude of a pulse in the Curr_Sample waveform.

The pulses are qualified or disqualified according to the evaluations at step 428. The pulses may be qualified or disqualified according to the evaluations in any suitable manner. According to one embodiment, a pulse that satisfies the above pulse qualification criteria is designated as qualified, and a pulse that fails to satisfy any of the above pulse qualification criteria is designated as non-qualified. After the pulses are qualified, the method ends.

Modifications, additions, or omissions may be made to the method without departing from the scope of the invention. The method may include more, fewer, or other steps. Additionally, steps may be performed in any suitable order without departing from the scope of the invention.

FIG. 6 is a flowchart illustrating one embodiment of a method for adjusting a saturation weight in accordance with a pulse quality metric. A pulse quality metric is a signal metric indicating the quality of one or more pulses. For example, a pulse quality metric may describe a characteristic such as pulse shape or beat-to-beat variability. A saturation weight may refer to a weight used for filtering saturation estimates. The metric may be used to adjust a saturation weight, which may enhance accuracy under conditions such as interference from a noise source, low perfusion, or electronic interference.

The method starts at step 450, where a saturation weight is established. The method may be applied to any suitable filter that filters saturation estimates. According to one embodiment, the filter may comprise a Kalman filter. For a Kalman filter, the saturation s may be updated for each sample from an estimation error P and Kalman gain K according to the following equation:

$$s_t = s_{t-1} + K_t(v_t - u_t s_{t-1})$$

where:

$$K_t = P_t u_t R_{t-1}^{-1}$$

$$P_t = ((P_{t-1} + Q)^{-1} + u_t^2 R_{t-1}^{-1})^{-1}$$

and u and v represent inputs, Q represents the variance of saturation s, and R represents the variance of noise. Inputs u and v may represent inputs calculated from the IR and Red plethysmographs utilizing coefficients defined by encoder 116. The ratio v/u may converge to the oxygen saturation estimate in the absence of artifacts.

According to one embodiment, noise variance R may be given by the following equation:

$$R = \left( \sum_{i=0}^{N-1} \frac{(v_{t-i} - u_{t-i} s_{t-i})^2}{N} \right)$$

where N represents a suitable number of samples, such as one pulse period or one second.

Saturation weight $w_t$ may be given by the following equation:

$$w_t = K_t \sum_{i=0}^{N-1} \frac{u_t^2}{N}$$

Saturation weight $w_t$ depends on Kalman gain K, which in turn depends on noise variance R. Accordingly, a change in the noise variance may yield a change in the saturation weight. Noise variance R may be dependent, at least in part, on the filtered saturation output of the Kalman filter.

A pulse quality metric is determined at step 462. The pulse quality metric Pulse_Qual may reflect the quality of the most recently evaluated pulse. According to one embodiment, the pulse quality metrics range from 0 to 1.

The saturation filtering may be in one of multiple response modes based on the response time of the filtering at step 466. As an example, the response modes may include a fast response mode, normal response mode, or slow response mode, where the fast response mode has a time of less than 4 seconds, normal response mode has a time of greater than 4 and less than 6, or slow response mode has a time of more than 6 seconds. The response mode may be user-selected or automatically selected.

If the saturation filtering is in a fast or a normal response mode at step 466, the method proceeds to step 468, where the noise variance is adjusted. According to one embodiment, the noise variance in the fast response mode may be adjusted according to the following equation:

$$R_t^{-1} = \left( \frac{b}{N} \sum_{i=0}^{N-1} u_{t-i}^2 \right)^{-1}$$

where b is a constant selected in accordance with the response mode. According to the embodiment, the noise variance in the normal response mode may be adjusted according to the following equation:

$$R_t^{-1} = \max\left( \min(R_{t-1}, \rho_{t-1}), \frac{b}{N} \sum_{i=0}^{N-1} u_{t-i}^2 \right)^{-1}$$

where ρ represents a second noise variance estimate. The second noise-variance estimate is designed to be less sensitive to rapid physiological saturation changes. If the saturation filtering is in the slow response mode at step 466, the method proceeds to step 470, where the noise variance is adjusted in accordance with pulse quality. According to one embodiment, the noise variance in the fast response mode may be adjusted according to the following equation:

$$R_t^{-1} = \max\left( \frac{\min(R_{t-1}, \rho_{t-1})}{temp^2}, \frac{b}{N} \sum_{i=0}^{N-1} u_{t-i}^2 \right)^{-1}$$

where:

$$temp = \max(\min(c_1 * Pulse\_Qual, c_2), c_3)$$

and $c_1$, $c_2$, and $c_3$ represent any suitable constants, for example, $c_1=2$, $c_2=1$, and $c_3=0.01$. According to the above equation, a change in pulse quality may yield a change in noise variance. As discussed above, a change in the noise variance may yield a change in the saturation weight. Accordingly, saturation weight may be adjusted in accordance with the pulse quality.

The saturation weight is adjusted in accordance with the noise variance c at step 474. After adjusting the saturation weight, the method ends.

Modifications, additions, or omissions may be made to the method without departing from the scope of the invention. The method may include more, fewer, or other steps. Additionally, steps may be performed in any suitable order without departing from the scope of the invention.

FIG. 7 is a flowchart illustrating another embodiment of a method for adjusting a saturation weight in accordance with a ratio-of-ratios variability metric and a pulse quality metric. A ratio-of-ratios variability metric indicates the variation of a ratio-of-ratios, where a ratio-of-ratios is the ratio of the absorbances of red and infrared signals. A pulse quality metric is a signal metric indicating the quality of one or more pulses. For example, a pulse quality metric may describe a characteristic such as pulse shape or beat-to-beat variability. A saturation weight may refer to a weight used for filtering saturation estimates. The metrics may be used to adjust a saturation weight, which may enhance accuracy under conditions such as interference from a noise source, low perfusion, or electronic interference.

The method starts at step 550, where a saturation weight is established. A ratio-of-ratios variability metric is determined at step 558. Any suitable ratio-of-ratios variability metric may be used. According to one embodiment, the ratio-of-ratios $\overline{RoR}$ may be determined from infrared and red input samples collected over a time period of any suitable duration, for example, less than 5 seconds, such as 3 seconds. $\overline{RoR}$ may be given by the following equation:

$$\overline{RoR} = \frac{\sum_{t=0}^{N-1}(IR_t * \text{Red}_t)}{\sum_{t=0}^{N-1} IR_t^2}$$

where Red represents red input values, IR represents infrared input values, and N represents the time period divided by the sample time.

According to the embodiment, a ratio-of-ratios variability metric RoR_Variance_Per may be given by the following equation:

$$\text{RoR\_Variance\_Per} = \sqrt{\frac{SumDiffSq}{\sum_{t=0}^{N-1} Red_t^2}}$$

where:

$$SumDiffSq = \sum_{t=0}^{N-1}(IR_t * \overline{RoR} - \text{Red}_t)^2$$

A pulse quality metric is determined at step 562. The pulse quality metric Pulse_Qual may reflect the quality of the most recently evaluated pulse.

The saturation filtering may be in one of multiple response modes based on the response time of the filtering at step 566. As an example, the response modes may include a fast response mode, normal response mode, or slow response mode. If the saturation filtering is in a fast or a normal response mode at step 566, the method proceeds to step 568, where the saturation weight is calculated from the ratio-of-ratios variance metric. According to one embodiment, the saturation weight may be adjusted by first calculating an intermediate value Sat_Noise_Per according to the following equation:

Sat_Noise_Per=RoR_Noise_Per*$d$Sat_$d$RoR where:

RoR_Noise_Per=RoR_Variance_Per*RoR where $$RoR = \frac{\sum_{t=0}^{N-1} R_t^2}{\sum_{t=0}^{N-1} IR_t^2}$$

and where dSat_dRoR represents the derivative of the saturation with respect to the ratio-of-ratios at a ratio-of-ratios value equal to RoR. This derivative may be calculated using the calibration coefficients selected by the oximeter based on the signals from the encoder 116. According to one embodiment, if Sat_Noise_Per is greater then a maximum threshold, Sat_Noise_Per may be set to a maximum value.

The saturation weight may be adjusted using the intermediate value Sat_Noise_Per. If Sat_Noise_Per is greater than a threshold $c_4$, such as $c_4$=0.09, then saturation weight may be adjusted according to the following equation:

$w_t = w_t * c_4 / \text{Sat\_Noise\_Per}$

According to the embodiment, before the first second of filtering has elapsed, the minimum filter weight $w_m$ may be set at $w_m$=1.0. Otherwise, minimum filter weight $w_m$ may be set at $w_m$=0.5 divided by the number of seconds. If the saturation filtering is in the slow response mode at step 566, the method proceeds to step 570, where the saturation weight is calculated from the ratio-of-ratios variance metric and then adjusted in accordance with the pulse quality metric. The saturation weight $w_t$ may be calculated in a manner similar to that of step 568, except that $w_t$ may be adjusted according to the pulse quality metric. For example, the equation for RoR_Noise_Per may be modified to:

RoR_Noise_Per=RoR_Variance_Per*RoR/temp where temp=max(min($c_1$*Pulse_Qual,$c_2$),$c_3$), and $c_1$, $c_2$, and $c_3$ represent any suitable constants, for example, $c_1$=2, $c_2$=1, and $c_3$=0.1.

Saturation is calculated at step 574. Saturation may be calculated according to the following equation:

Saturation$_t$=$w_t$*Raw_Saturation$_t$+(1−$w_t$)*Saturation$_{t-1}$ where Raw_Saturation$_t$ is calculated from $\overline{RoR}$ using the calibration coefficients selected by the oximeter based on the signals from the encoder 116. After calculating the saturation, the method ends.

Modifications, additions, or omissions may be made to the method without departing from the scope of the invention. The method may include more, fewer, or other steps. Additionally, steps may be performed in any suitable order without departing from the scope of the invention.

As an example, the above-described saturation weight might be used to filter the ratio-of-ratios prior to saturation calculation, rather than calculating saturation first and then filtering the ratio-of-ratios. According to one embodiment, a ratio-of-ratios weight may be established in accordance with the ratio-of-ratios variability metric and the pulse quality metric. The ratio-of-ratios weight may be established in a manner similar to that of step 570. The ratio-of-ratios may be filtered in accordance with the ratio-of-ratios weight, and the saturation calculated according to the filtered ratio-of ratios.

Certain embodiments of the invention may provide one or more technical advantages. A technical advantage of one embodiment may be that a noise gate parameter of a noise gate criterion may be adjusted in accordance with an ensemble averaging weight. Ensemble averaging filtering may reduce the noise level, which may allow for a lowered noise gate. Accordingly, the ensemble averaging weight, which indicates the degree of ensemble averaging, may be used to adjust the noise gate parameter.

Another technical advantage of one embodiment may be that a pulse period criterion may be adjusted in accordance with an ensemble averaging weight. According to the embodiment, an ensemble averaging weight may indicate that a qualified pulse is not likely to have a pulse period that is substantially shorter than an average pulse period. Accordingly, a pulse period criterion may be adjusted to disqualify a pulse having a pulse period that is substantially shorter than an average pulse period.

Another technical advantage of one embodiment may be that a pulse amplitude criterion may be adjusted in accordance with an average pulse amplitude and an average pulse period. According to one embodiment, a pulse amplitude criterion may disqualify a pulse with an amplitude that is much smaller than (e.g., more than three times smaller) an average amplitude and a period that is much greater that an average period. The pulse amplitude criterion may reduce the likelihood of qualifying instrument noise when the pulse amplitude suddenly disappears.

Another technical advantage of one embodiment may be that a saturation weight may be adjusted in accordance with a ratio-of-ratios variability metric and a pulse quality metric. The metrics may be used to adjust a saturation weight, which may enhance accuracy under conditions such as motion artifact, low perfusion, or electronic interference.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for calculating a physiological parameter, comprising:
   receiving, via a processor, a signal representing a plurality of pulses, the signal generated in response to detecting light scattered from blood perfused tissue;
   determining, via the processor, an ensemble averaging weight for an ensemble averaging filter;
   adjusting, via the processor, a pulse qualification criterion in accordance with the ensemble averaging weight, the pulse qualification criterion for qualifying a pulse;
   evaluating, via the processor, the plurality of pulses according to the pulse qualification criterion to determine one or more qualified pulses of the plurality of pulses;
   ensemble averaging, via the ensemble averaging filter, the one or more qualified pulses of the plurality of pulses using the ensemble averaging weight;
   calculating, via the processor, a physiological parameter based at least in part upon one or more ensemble averaged pulses; and
   outputting, via the processor, the physiological parameter for display.

2. The method of claim 1, wherein adjusting the pulse qualification criterion comprises reducing a noise gate level when the ensemble averaging weight is below a threshold.

3. The method of claim 1, wherein:
   adjusting a pulse qualification criterion in accordance with the ensemble averaging weight comprises adjusting, via the processor, a pulse period threshold to disqualify a pulse having a pulse period that is substantially shorter than an average pulse period.

4. The method of claim 1, wherein evaluating the plurality of pulses in accordance with the pulse qualification criterion comprises applying a trained neural net to the plurality of pulses to determine the one or more qualified pulses.

5. The method of claim 1, wherein the pulse qualification criterion comprises a threshold for a signal metric of the signal.

6. The method of claim 5, wherein the signal metric comprises amplitude, period, pulse shape, ratio-of-ratios, or rise time.

7. A system configured to calculate a physiological parameter, comprising:
   an interface configured to:
      receive a signal representing a plurality of pulses, the signal generated in response to detecting light scattered from blood perfused tissue;
   an ensemble averaging filter configured to filter the signal; and
   a processor configured to:
      determine an ensemble averaging weight for the ensemble averaging filter;
      adjust a pulse qualification criterion in accordance with the ensemble averaging weight, the pulse qualification criterion for qualifying a pulse; and
      evaluate the plurality of pulses according to the pulse qualification criterion to determine one or more qualified pulses of the plurality of pulses;
   wherein the ensemble averaging filter is configured to ensemble average the one or more qualified pulses of the plurality of pulses using the ensemble averaging weight, and the processor is configured to calculate a physiological parameter based at least in part upon one or more ensemble averaged pulses and output the physiological parameter for display.

8. The system of claim 7, wherein the processor is configured to adjust the pulse qualification criterion by reducing a noise gate level when the ensemble averaging weight is below a threshold.

9. The system of claim 7, the processor further configured to:
   adjust a pulse qualification criterion in accordance with the ensemble averaging weight by adjusting a pulse period threshold to disqualify a pulse having a pulse period that is substantially shorter than an average pulse period.

10. The system of claim 7, wherein the processor is configured to apply a trained neural net to the plurality of pulses to determine the one or more qualified pulses.

11. The system of claim 7, wherein the pulse qualification criterion comprises a threshold for a signal metric of the signal.

12. The system of claim 11, wherein the signal metric comprises amplitude, period, pulse shape, ratio-of-ratios, or rise time.

13. A system for calculating a physiological parameter, comprising:
   means for receiving a signal representing a plurality of pulses, the signal generated in response to detecting light scattered from blood perfused tissue;
   means for determining an ensemble averaging weight for an ensemble averaging filter;
   means for adjusting a pulse qualification criterion in accordance with the ensemble averaging weight, the pulse qualification criterion for qualifying a pulse;
   means for evaluating the plurality of pulses according to the pulse qualification criterion to determine one or more qualified pulses of the plurality of pulses;
   means for ensemble averaging the one or more qualified pulses of the plurality of pulses using the ensemble averaging weight;
   means for calculating a physiological parameter based on one or more ensemble averaged pulses; and
   means for outputting the physiological parameter for display.

14. The system of claim 13, wherein the means for adjusting a pulse qualification criterion comprises means for reducing a noise gate level when the ensemble averaging weight is below a threshold.

15. The system of claim 13, wherein the pulse qualification criterion comprises a threshold for a signal metric of the signal.

16. The system of claim 15, wherein the signal metric comprises amplitude, period, pulse shape, ratio-of-ratios, or rise time.

17. A system configured to calculate a physiological parameter, comprising:
  an interface configured to:
    receive a signal representing a plurality of pulses, the signal generated in response to detecting light scattered from blood perfused tissue;
  an ensemble averaging filter configured to filter the signal; and
  a processor configured to:
    determine an ensemble averaging weight for the ensemble averaging filter;
    adjust one or more pulse qualification criteria in accordance with the ensemble averaging weight, a pulse qualification criterion for qualifying a pulse, the one or more pulse qualification criteria adjusted by:
      reducing a noise gate level of a noise gate criterion based at least in part on the ensemble averaging weight; and
      adjusting a pulse period criterion to disqualify a pulse having a pulse period that is substantially shorter than an average pulse period; and
    evaluate the plurality of pulses according to the one or more pulse qualification criteria to determine one or more qualified pulses of the plurality of pulses, wherein the ensemble averaging filter is configured to ensemble average the one or more qualified pulses using the ensemble averaging weight, and the processor is configured to calculate a physiological parameter based at least in part on one or more ensemble averaged pulses and to output the physiological parameter for display.

18. The system of claim 17, wherein the signal metric comprises amplitude, period, pulse shape, ratio-of-ratios, or rise time.

19. The system of claim 18, wherein the one or more pulse qualification criteria comprise a threshold for a signal metric of the signal.

20. The system of claim 19, wherein the signal metric comprises amplitude, period, pulse shape, ratio-of-ratios, or rise time.

* * * * *